(12) United States Patent
Hamann (10) Patent No.: US 10,045,759 B2
(45) Date of Patent: Aug. 14, 2018

(54) EPICUTANEOUS PATCH TEST CHAMBER

(75) Inventor: Curtis P. Hamann, Paradise Valley, AZ (US)

(73) Assignee: SmartHealth, Inc., Phoenix, AZ (US)

( * ) Notice: Subject to any disclaimer, the term of this patent is extended or adjusted under 35 U.S.C. 154(b) by 2307 days.

(21) Appl. No.: 12/765,051

(22) Filed: Apr. 22, 2010

(65) Prior Publication Data

US 2011/0264003 A1    Oct. 27, 2011

(51) Int. Cl.
*A61B 10/00*    (2006.01)
(52) U.S. Cl.
CPC ................. *A61B 10/0035* (2013.01)
(58) Field of Classification Search
CPC .................................................. A61B 10/0035
USPC ...... 600/556; 602/41–59; 604/304, 305, 308
See application file for complete search history.

(56) References Cited

U.S. PATENT DOCUMENTS

| | | |
|---|---|---|
| 2,235,436 A | 3/1941 | Laub |
| 2,841,138 A | 7/1958 | Laub |
| 3,515,126 A | 6/1970 | Fregert |
| 3,703,890 A | 11/1972 | Saunders, Jr. |
| 3,870,593 A | 3/1975 | Elton et al. |
| 3,894,531 A | 7/1975 | Saunders, Jr. |
| 4,158,359 A | 6/1979 | Kurokawa et al. |
| 4,214,592 A | 7/1980 | Jacquet et al. |
| 4,265,234 A | 5/1981 | Schaar |
| 4,341,208 A | 7/1982 | Gordon |
| 4,450,844 A | 5/1984 | Quisno |
| 4,450,845 A | 5/1984 | Engel |
| 4,472,507 A | 9/1984 | Pluim, Jr. |
| 4,473,083 A | 9/1984 | Maganias |
| 4,543,964 A | 10/1985 | Breneman |
| 4,600,001 A | 7/1986 | Gilman |
| 4,614,183 A | 9/1986 | McCracken et al. |
| 4,619,253 A | 10/1986 | Anhäuser et al. |
| 4,765,986 A | 8/1988 | Liedtke |
| 4,788,971 A | 12/1988 | Quisno |
| 4,809,707 A | 3/1989 | Kraft et al. |
| 4,887,611 A | 12/1989 | Rüdiger et al. |
| 4,915,102 A | 4/1990 | Kwiatek et al. |
| 5,044,372 A | 9/1991 | Anhäuser et al. |

(Continued)

FOREIGN PATENT DOCUMENTS

| | | |
|---|---|---|
| DE | 3811564 A1 | 10/1989 |
| EP | 0 335 231 A2 | 10/1989 |

(Continued)

OTHER PUBLICATIONS

Finn Chambers; Patch Testing, pamphlet, known prior to Apr. 22, 2010, 1 page.

(Continued)

*Primary Examiner* — Rene Towa
*Assistant Examiner* — H. Q. Nguyen
(74) *Attorney, Agent, or Firm* — Reinhart Boerner Van Deuren P.C.

(57) ABSTRACT

A test chamber for epicutaneous patch test units is provided. The test chamber is formed of a multilayer material including at least one absorbent layer and at least one barrier layer. The test chamber is adapted to contain a liquid or petrolatum-based allergen. The absorbent layer absorbs the liquid or petrolatum-based allergen, while the barrier layer prevents the allergen from migrating out of the test chamber.

37 Claims, 4 Drawing Sheets

(56) References Cited

U.S. PATENT DOCUMENTS

| | | |
|---|---|---|
| 5,325,864 A | 7/1994 | Gerber |
| 5,874,226 A | 2/1999 | Zeytinoglu et al. |
| 5,994,662 A | 8/1999 | Schoendorfer |
| 6,107,536 A * | 8/2000 | Dadinis .......................... 602/41 |
| 6,142,954 A | 11/2000 | Anhäuser et al. |
| 6,143,945 A | 11/2000 | Augustine et al. |
| RE37,934 E | 12/2002 | Hoffmann |
| 2005/0043648 A1 | 2/2005 | Niklasson |

FOREIGN PATENT DOCUMENTS

| | | |
|---|---|---|
| NL | 8701577 A | 2/1989 |
| WO | WO 94/14062 | 6/1994 |
| WO | WO 94/17735 A1 | 8/1994 |
| WO | WO 97/24987 | 7/1997 |
| WO | WO 99/08601 A1 | 2/1999 |

OTHER PUBLICATIONS

Allergeaze; Patch Test Chamber; pamphlet; known prior to Apr. 22, 2010, 2 pages.

Products for Dermatology; Curatest, pamphlet; known prior to Apr. 22, 2010, 6 pages.

Dormer Laboratories, Inc., IQ-Ultra Product Information; pages printed from a website; http://www.dormer.ca/Phy_Pages/IQ_Prod.aspx; date last visited Jan. 25, 2010, 2 pages.

\* cited by examiner

EPICUTANEOUS PATCH TEST CHAMBER

FIELD OF THE INVENTION

This invention generally relates to patch test units, particularly epicutaneous allergy patch test chambers.

BACKGROUND OF THE INVENTION

Epicutaneous patch test units are used for skin tests to determine and diagnose causes of allergic contact dermatitis. The patch test units used for liquid or petrolatum based allergens typically include an absorbent pad for absorbing the allergen. Some patch test units include at least one test chamber holding the absorbent pad. The test chambers are arranged on a patch test tape coated with a hypoallergenic adhesive for holding the test chambers on test subject's skin. In other test units, the absorbent pads are arranged directly on the patch test tape without a chamber.

Typically, allergens are loaded in a syringe and carefully injected into the test chambers or directly onto the absorbent pads, in an appropriate quantity. The liquid or petrolatum based allergens are absorbed by the absorbent pad. The patch test unit loaded with the allergens is then applied on the back or other appropriate areas of the test subject's skin, such that the allergens can come in contact with the skin. The test unit is then removed after a predetermined time. The first reading or observation of the test subject's reaction to the allergens takes place immediately after the removal of the test unit and further readings or observations can occur at given intervals of time.

Some patch test units include test chambers that are formed of an aluminum, polyethylene, or polyurethane or other polymer blend. Typically, the test chambers include a reservoir for holding allergens. Some patch test units require a tester to place an absorbent pad in the test chamber at the time of testing. The loose absorbent pad can be easily forgotten. Further, placing of the absorbent pad in the test chamber can often be a tedious and time-consuming process for the tester. As some liquid allergens must be placed in the patch test unit immediately before being applied on the test subject to avoid evaporation of the liquid allergen, such time consuming set up process is undesirable and can negatively impact test results. Further, the loose absorbent pads may become displaced during the patch testing or fall out from the test chamber during preparation, thereby posing a risk of contamination. Other patch test units that include absorbent pads without test chambers also present contamination risks. The patch test units available in the market include, but not limited to, Finn Chambers®, allegEAZE™, Van der Bend Chambers, IQ® and IQ-Ultra® chambers, Curatest® and Curatest® F patch test strips, and Torii patches.

The Finn Chambers® test units, which is available through the assignee of the present application, include aluminum test chambers. To use Finn Chambers® for liquid allergens, the tester must place an absorbent pad in the form of a loose filter paper disc in the aluminum chamber. The loose filter paper disc can present a number of challenges. First, placing the small and thin loose filter paper disc in a small chamber (typically 8 mm or 12 mm in diameter) can be a tedious and time-consuming process. Further, as the filter paper disc is held in place only by a surface tension of the wet filter paper disc holding a liquid allergen, the filter paper disc can easily be displaced or slide out from the center of the chamber, for example, when the test unit is vertically lifted to be applied on the test subject. Sometimes, the filter paper disc may even be displaced from the chamber by test subject's movements during a test period (typically 48 hours.) Further, the aluminum chambers may interact with mercurial compounds or other allergens leading to potential false patch test readings.

The allegEAZE™ patch test systems are also available through the assignee of the present application. The allegEAZE™ patch test systems include injection molded plastic test chambers. This plastic test chamber has a filter paper absorbent pad pressed into the chamber base. Customers of the allegEAZE™ patch test systems have complained that the filter paper absorbent pads often fall out prior to testing. Sometimes, the filter paper absorbent pads are displaced from the test chambers while still in a box and are missing when the patch test system is removed from the box. Because the filter paper absorbent pads are mechanically forced into the test chamber, even if the displaced filter paper absorbent pad is found in the box, it is difficult to correctly place the pad back into the test chamber. If the displaced filter paper absorbent pads are completely missing, the customers either have to discard the whole patch test system, or use them with some test chambers missing the absorbent pad as no extra absorbent pads are provided with the test systems. Such patch test systems are described in Diagnostic Testing Device for the Skin, U.S. Pat. No. 5,325,864, the entire disclosure of which is incorporated herein by reference thereto.

The Van der Bend also has test chambers similar to the allegEAZE™ test chambers, and thus, has the similar missing absorbent pad problems. Dutch Patent No. 8701577 to Van der Bend, the entire disclosure of which is incorporated herein by reference thereto, discloses patch test unit including absorbent pads, which has the similar missing absorbent pad problems.

The IQ-Ultra® patch test units from Chemotechnique MB Diagnostics does not have a true test chamber like the previously described aluminum or plastic test chambers. Rather, IQ-Ultra® patch test unit's reservoir for holding an allergen is provided by a negative space created by a thickness of a square-shaped frame formed of a polymeric foam material, which is arranged on a square-shaped filter element that is secured between a patch test tape and the foam frame. Since the filter element is fixed with adhesives, there is no risk of the filter element being displaced as it was with the previously described test chambers. However, the problem with the IQ-Ultra® is that the square foam frame, which is covered with an adhesive, absorbs the liquid allergen and/or allows the liquid allergen to flow under the foam, thereby contaminating neighboring chambers and/or preventing the allergen from contacting the skin when placed on the test subject. Further, the test chamber is too deep for the allergen absorbed in the filter paper to come in contact with the patient's skin. These test chambers absorb the allergen but do not release sufficiently for accurate testing. Such patch test units are described in Epicutaneous Test Plaster, U.S. Patent Publication No. 2005/0043648, the entire disclosure of which is incorporated herein by reference thereto.

The Curatest® and Curatest® F patch test strips from Lohmann GmbH do not include a true test chamber or a negative space sufficient for a reservoir. These test strips include absorbent pads secured between a patch test tape and a thin plastic ring overlaying the periphery of the absorbent pad. The thin plastic ring is formed of a thin plastic film, thus it provides hardly any negative space. Therefore, the allergen absorbed in the absorbent pad can smear beyond the plastic ring during the test period. Further, the surface area of the absorbent pad exposed to the patient is substantially reduced by the plastic ring to reduce an amount of the allergen that comes in contact with the test subject. Such patch test strips are described in Epicutaneous Test Plaster, U.S. Pat. No. 5,044,372; and Epicutaneous Test Plaster, U.S. Pat. No. 6,142,954; the entire disclosures of which are incorporated herein by reference thereto.

The Torii test patch units have absorbent pads arranged on a patch test tape without a test chamber or a ring cover. There is no negative space reservoir to contain allergens, thus, the allergens can smear beyond the absorbent pads to cause contamination. Further, users of the Torii test patch units including cotton absorbent pads have reported problems with irritations from cotton threads which begin to fray before and/or during testing, thereby resulting in false readings.

There exists, therefore, a need in the art for an improved epicutaneous patch test chamber for liquid or petrolatum-based allergens. The invention disclosed herein provides an improved test chamber and method of making the test chamber. These and other advantages of the invention, as well as additional inventive features, will be apparent from the description of the invention provided herein.

BRIEF SUMMARY OF THE INVENTION

In view of the above, embodiments of the present invention provides a new and improved epicutaneous patch test unit that overcomes one or more of the problems existing in the art. More particularly, embodiments of the present invention provide a new and improved epicutaneous patch test unit including a test chamber having an integrally formed absorbent layer.

In one embodiment, a single piece epicutaneous test chamber is provided. The single piece test chamber includes a reservoir and a ridge, which are formed as one continuous piece. The reservoir has an inner surface formed of an absorbent material.

In another embodiment, an epicutaneous test chamber formed of a multilayer material is provided. The test chamber includes a reservoir and a ridge. The reservoir and the ridge are integrally formed of the multilayer material including at least one absorbent layer and at least one barrier layer.

In yet another embodiment, a paper test chamber for an epicutaneous patch test is provided. The paper test chamber includes a ridge and a reservoir. The ridge includes an inner side, a top edge, and an outer side, and the reservoir is defined by a chamber base and the inner side of the ridge. The chamber base, the inner side, the top edge, and the outer side are formed of a paper.

In another embodiment, an epicutaneous patch test unit is provided. The patch test unit includes a patch test tape and at least one test chamber arranged on the patch test tape. The at least one test chamber is formed of a multilayer material including an absorbent layer, and includes a reservoir and a ridge.

The patch test tape can include an adhesive layer formed of a skin contact grade adhesive. The epicutaneous patch test unit can include a plurality of the test chambers arranged on top of the adhesive layer. The patch test unit including the plurality of the test chambers loaded with allergens are placed on a test subject such that the ridge touches the test subject's skin. The adhesive layer adheres to test subject's skin and holds the test chambers in place against test subject's skin. The ridge is configured to retain a shape to continuously provide the barrier against the test subject's skin to contain the allergen within the reservoir. The test chamber is configured to retain its shape when dampened and/or under contact pressure.

Any of the test chambers discussed above can be formed of a multilayer material including at least one absorbent layer and at least one barrier layer, wherein the at least one absorbent layer and the at least one barrier layer are bonded by at least one adhesive layer. In such embodiments, one of the at least one absorbent layer defines the inner surface of the reservoir to absorb, hold, and release a liquid or petrolatum-based allergen, while the barrier layer contains the allergen within the reservoir and provides a structural support. The barrier layer is also a vapor barrier that is preferably formed of a moisture resistant plastic material.

Any of the test chambers discussed above can be formed of a multilayer material including an absorbent layer formed of a cellulose fiber material having a thickness of between 0.006" and 0.0010", an adhesive layer formed of a medical grade hypoallergenic adhesive having a thickness of between 0.001" and 0.002", and a barrier layer formed of a polyolefin material having a thickness of between 0.005" and 0.008". Such test chambers can provide a reservoir having a depth of between 0.33 mm to 0.55 mm; wherein the reservoir is configured to hold a volume between 20 μl and 33 μl. The polyolefin material is inert, and provides a structural support to retain the shape of the test chamber and creates a vapor barrier both ways. In other embodiments, the barrier layer can be formed of metal foils, polyethylene coated or acrylate based films, UV coated films, etc. The test chambers can also be configured to have various different depth and volume reservoirs.

Any of the test chambers discussed above includes an absorbent layer that absorbs a liquid allergen loaded in the reservoir. Further, the test chambers can also include a barrier layer, which contains the liquid allergen within the reservoir and prevents the liquid allergen from escaping through chamber walls and the patch test tape.

Any of the test chambers discussed above can include a ridge including an inner side, a top edge, and an outer side, and a reservoir defined by a chamber base and the inner side of the ridge. In such test chambers, the inner side extends from the chamber base vertically or canted, and the top edge is formed on the end of the inner side opposite from the chamber base. The ridge is configured to retain a shape against a test subject's skin during a test period to contain an allergen within the reservoir.

Any of the test chambers discussed above including an absorbent layer can be formed to include the reservoir having a depth of between 1 to 3 times a thickness of the absorbent layer. The test chamber can also be formed to include the reservoir having a depth between 0.3 to 1.5 times a thickness of the multilayer material forming the test chamber.

Any of the test chambers discussed above can be formed to include the ridge having a circular shape, a rectangular shape, a square shape, a triangular shape or other shapes.

Any of the test chambers discussed above can include a reservoir and a ridge, which are formed of one continuous piece of a multilayer material having at least one absorbent layer, wherein one of the at least one absorbent layer defines an inner surface of the reservoir. The absorbent layer is formed of a absorptive fiber material that can absorb, retain, and release allergens. The reservoir is adapted to contain a liquid or petrolatum-based allergen. The ridge is configured to temporarily indent a test subject's skin when the test chamber is placed on the test subject with a light pressure and contain the allergen within the reservoir against the test subject's skin during a 48 hour test period. The ridge confirms good skin occlusion on the test subject.

Any of the test chambers discussed above can be formed of a multilayer material including an absorbent layer, an adhesive layer, and a barrier layer, wherein the absorbent layer is permanently bonded to the barrier layer via the adhesive layer. The absorbent layer defines the inner surface of the reservoir and a top surface of the ridge, wherein the top surface of the ridge contacts test subject's skin when the test chamber is applied on the test subject. The barrier layer defines an outer surface of the reservoir, which is adhered to a patch test tape.

Any of the test chambers discussed above can have a reservoir having a flat-bottom shape. The test chamber can include a chamber base, an inner side, a top edge, and an outer side, which are continuously formed of a multilayer material including an absorbent layer and a barrier layer. The outer side extends vertically down from the top edge such that the barrier layer of the inner side and the barrier layer of the outer side face each other, wherein the absorbent layer defines an outer surface of the outer side.

In yet another embodiment, a method of making an epicutaneous test chamber is provided. The method includes steps of providing a multilayer material, cutting the multilayer material, and press forming the multilayer material to provide a test chamber including a reservoir and a ridge.

Providing a multilayer material can involve laminating an absorbent material and a barrier material with an adhesive to provide a three layer material having the absorbent layer, the adhesive layer, and the barrier layer. The three layer material can be provided in a roll form or a sheet.

Cutting the multilayer material can involve punch cutting and/or die cutting a flat disc from the three layer material. The flat disc is then press embossed using a forming tool set. The forming tool set press embosses a center area of the flat disc to provide a sunken negative space forming the reservoir. The pressed center area of the flat disc forms a flat bottomed chamber base and an inner side defining the reservoir, wherein the absorbent layer forms an inner surface of the reservoir. Further, a portion of the flat disc forming the inner side is folded over to form the ridge including a top edge and an outer side.

Punch cutting can provide a circular flat disc and press embossing the circular flat disc provides the test chamber having a circular ridge. Or a rectangular flat disc can be punch cut and press embossed to provide the test chamber having a rectangular ridge. Alternatively, a triangular flat disc can be punch cut and press embossed to provide the test chamber having a triangular ridge. Similarly, the test chamber can be formed to have various different shapes.

In some embodiments, the multilayer material is press formed and subsequently cut to form the test chamber. Alternatively, the multilayer material can be press formed and cut simultaneously to form the test chamber. The multilayer material can be provided by laminating at least one layer of paper and at least one layer of plastic material.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Various embodiments of the present invention provide new and improved epicutaneous patch test units including embossed paper test chambers. The paper test chamber according to embodiments of the present invention solves aforementioned problems of the conventional test chamber by providing a one-piece test chamber formed of a multilayer material including at least one layer of suitable absorbent material, which serves as a carrier of liquid and petrolatum-based allergen. Further, the test chamber including the absorbent layer is configured to hold and/or absorb and release allergens such as petrolatum-based and liquid allergens.

Figure 1:
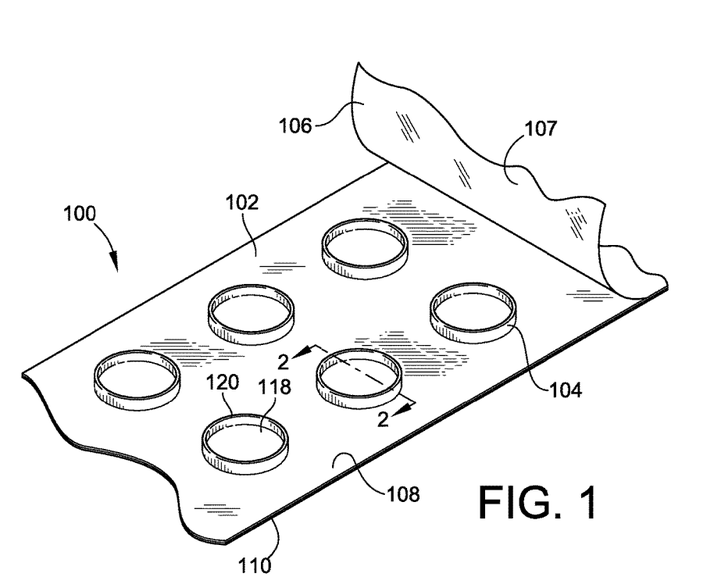
FIG. 1 is a perspective view of a epicutaneous patch test unit including a plurality of test chambers, a patch test tape and a cover sheet according to an embodiment of the present invention.

FIG. 1 illustrates an epicutaneous patch test unit 100 according to an embodiment of the present invention. The test unit 100 generally includes a patch test tape 102, a plurality of test chambers 104, and a cover sheet 106. The patch test tape 102 includes an adhesive layer 108 and a substrate layer 110. The plurality of the test chambers 104 are arranged on the top of the adhesive layer 108 and secured to the patch test tape 102 via the adhesive layer 108. Depending on an application, the patch test unit 100 can include one chamber or more than one chamber. Preferably, the patch test unit 100 includes twelve or less chambers 104. The cover sheet 106 is arranged over the plurality of chambers 104 and covers the plurality of chambers 104. A surface 107 of the cover sheet 106 is preferably coated with a release coating, for example a silicone release coating, such that the cover sheet 106 is releaseably attached to the adhesive layer 108.

Figure 6:
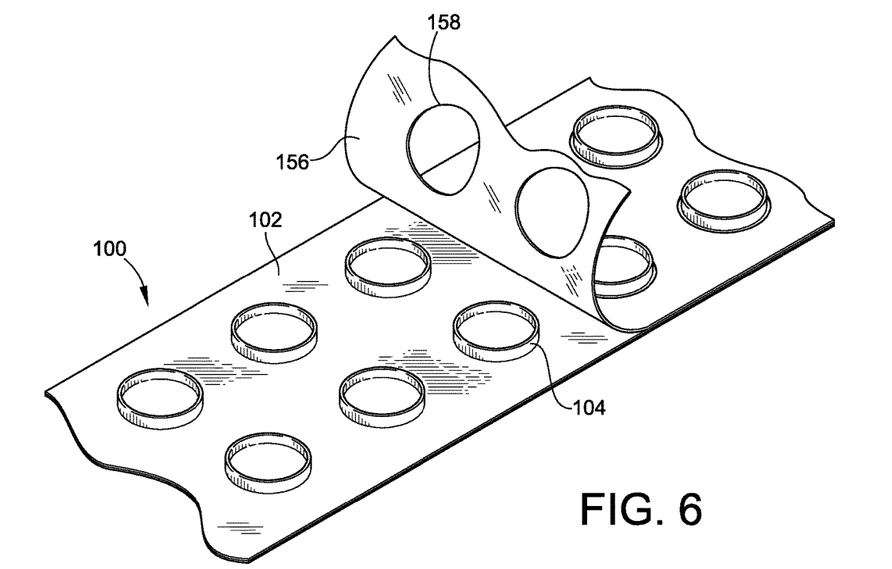
FIG. 6 is a perspective view of a epicutaneous patch test unit including a plurality of test chambers, a patch test tape and a cover sheet having openings to expose the test chambers according to a different embodiment of the present invention.

In some embodiments, the cover sheet can have openings to expose the test chambers. As shown in FIG. 6, the patch test unit 100 can include a cover sheet 156 that includes multiple openings 158. The openings 158 are die cut according to the shape and size of the test chambers 104, such that a diameter of the opening 158 is slightly greater than the outer diameter of the test chamber 104 to provide a sufficient clearance for smooth detachment of the cover sheet 156. Such cover sheet 156 allows a tester to load the test chambers with allergens without removing the cover sheet 156 until ready to place on a test subject. The test subject can be a human or an animal as used herein, and can also be referred to as a patient or other similar terms. The cover sheet 156 can reduce a risk of contamination by preventing accidental spills or drippings of allergen on the patch test tape 102 during the loading process, and better preserve patch test tape adhesion by delaying exposure of patch test tape adhesive until the time of application.

The patch test unit 100 may be sold with a predetermined number of test chambers 104 assembled on the patch test tape 102. Alternatively, the test chambers 104 may be arranged on the patch test tape 102 at a test site, wherein a tester places a desired number of test chambers 104 on the patch test tape 102. The patch test tape 102 may also be cut to a desired length according to the number of test chambers 104 required for a test.

Figure 2:
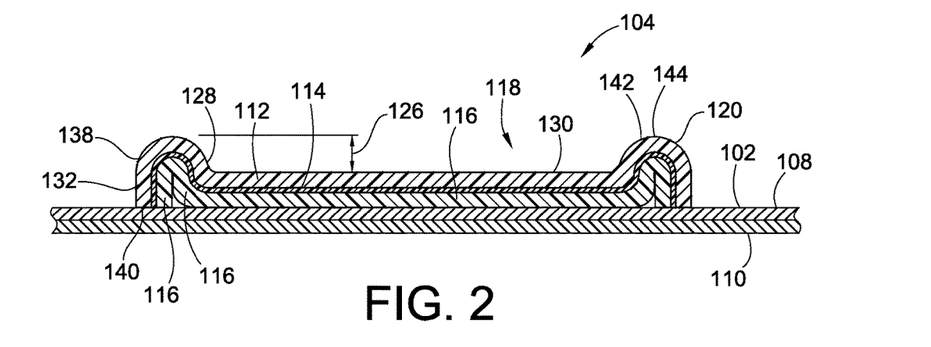
FIG. 2 is a schematic cross-sectional side view of the test chamber of FIG. 1 including a paper layer, an adhesive layer and a barrier layer.

FIG. 2 shows a cross-sectional view of the test chamber 104 on the patch test tape 102 cut at 2 (FIG. 1.) As shown, the test chamber 104 is a one-piece test chamber, which is formed from a multilayer material 132 (FIGS. 2 and 4) including an absorbent layer 112, an adhesive layer 114, and a barrier layer 116. The one-piece test chamber refers to a test chamber that is formed as a single, integral piece, wherein all parts of the test chamber are integrally formed as one continuous piece from a single multilayer material rather than an assembly of individual parts. The one-piece test chamber is also referred to herein as a single piece test chamber, an integrally formed test chamber or other similar terms.

The one-piece test chamber 104 can be formed via a conventional forming process, such as embossing or molding. Since the test chamber 104 is formed from a multilayer material 132 including the absorbent layer 112, the test chamber 104 does not require a separate absorbent pad. The absorbent layer 114 cannot be separated from the test chamber 104 without destroying the test chamber 104.

In this embodiment, the test chamber 104 is formed by press embossing the multilayer material 132 to create a negative space that defines a reservoir 118 for holding an allergen. The test chamber 104 also includes a ridge 120, which is integrally formed with the reservoir 118 during embossing. The ridge 120 is configured to retain its shape against the patient's skin during a test period to maintain an optimal occlusion of the allergen against the skin and to minimize or eliminate migration of allergen between test chambers. Thus, the ridge 120 is rigid enough to temporarily indent the skin and seal the test chamber 104 against the skin during the test period (typically 48 hours) to prevent spreading of the allergen beyond the defined area of the test chamber 104.

The absorbent layer 112 can be formed of any suitable paper or fiber materials that can function as an absorbent for an allergen. For example, the absorbent layer 112 may be formed of a medical grade or hypoallergenic cellulose fiber material or filter paper-like material having a thickness of between 0.002" and 0.020", preferably between 0.004" and 0.012", and more preferably between 0.006" and 0.010". The absorbent layer 112 is configured to absorb and retain a liquid allergen and release the allergen when applied on the test subject. The release of the allergen is triggered, for example, by perspiration or body temperature of the test subject.

The adhesive layer 114 can be formed of any suitable adhesive. For example, the adhesive layer 114 can be formed of a medical grade hypoallergenic adhesive having a thickness of between 0.0005" and 0.005", preferably between 0.001" and 0.003", and more preferably between 0.001" and 0.002".

The barrier layer 116 can be formed of any suitable material such a plastic, aluminum, or metallic material. Preferably, the barrier layer 116 is formed of an inert polymeric material such as polyethylene, polyester, polypropylene, etc., which can provide a structural support to retain the shape of the test chamber 104 and create a vapor barrier both ways. Other suitable materials for the barrier layer 116 includes, but not limited to, a metal foil, a polyethylene coated film, an acrylate based film, and an UV coated film. In one embodiment, the barrier layer 116 is formed of an inert polyolefin material having a thickness of between 0.003" and 0.015", preferably between 0.004" and 0.010", and more preferably between 0.005" and 0.008". The barrier layer 116 is flexible enough to be press formed without breaking and sufficiently rigid to retain the shape of the test chamber 104 throughout the test period.

As shown in FIG. 2, the test chamber 104 includes a chamber base 130 and the ridge 120. The chamber base 130 and the ridge 120 are integrally formed when the multilayer material 132 is press embossed or molded to form the reservoir 118. The ridge 120 includes an inner side 128, an outer side 138, and a top edge 142. The chamber base 130 and the inner side 128 define the reservoir 118, wherein chamber base 130 is the horizontal bottom surface of the reservoir 118 and the inner side 128 is the wall of the reservoir 118. In this embodiment, the inner side 128 extends vertically from the chamber base 130. In other embodiments, the inner side 128 may extend vertically and axially such that the inner side 128 extends canted from the chamber base 130.

The top edge 142 is formed at an end of the inner side 128 opposite the end that meets the chamber base 130. The top edge 142 has a rounded top surface 144, which is formed when a portion of the multilayer material 132 forming the ridge 120 is folded over such that the barrier layer 116 of the inner side 128 faces the barrier layer 116 of the outer side 138. As such, the outer side 138 vertically extends down from the top edge 142 to the patch test tape 102. In this embodiment, the inner side 128 abuts the outer side 138. However, in other embodiments, the inner side 128 and the outer side 138 may form an angle between them such that they do not continuously abut each other. Further, the outer side 138 may be much shorter than the inner side 128 in some embodiments, such that the end 140 of the outer side 138 do not touch the patch test tape 102.

The test chamber 104 is a single piece device wherein all parts of the test chamber 104 are formed from the one continuous multilayer material 132. Thus, all parts of the test chamber 104 including the chamber base 130, the inner side 128, the top edge 142, and the outer side 138 are one continuous piece formed of the multilayer material 132 having the absorbent layer 112, the adhesive layer 114, and the barrier layer 116. Therefore, the test chamber 104 according to embodiments of the present invention is a single piece device, unlike prior test chambers which are an assembly of a separate base piece and a separate wall piece, or an assembly of a separate chamber piece and a separate filter paper piece, etc.

Figure 3:
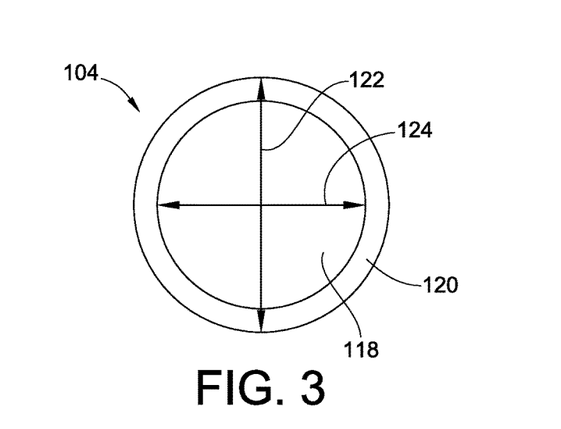
FIG. 3 is a schematic top view of the test chamber of FIGS. 1 and 2.

FIG. 3 is a top view of the test chamber 104 of FIGS. 1 and 2. As shown, the test chamber 104 has a circular shape. In other embodiments, the chamber 104 can be formed into various different shapes such as a rectangle, square, triangle, etc. The test chamber 104 can be configured in various sizes. For example, the test chamber 104 can be formed to have an inner diameter 124 of 8 mm, 12 mm, or 18 mm.

In one embodiment, the test chamber 104 is formed of the multilayer material 132 comprising a laboratory grade cellulose fiber material layer 112 having a thickness of about 0.008" (0.2032 mm), a medical grade hypoallergenic adhesive layer 114 that meets the guidelines for skin contact devices having a thickness of about 0.0015" (0.0381 mm), and a white matte polyolefin material layer 116 having a thickness of about 0.0065" (0.1651 mm). The chamber 104 can be configured to have a depth 126 of between about 0.05 to 5 times a total thickness of the multilayer material 132, preferably between about 0.1 to 1 times a total thickness of the multilayer material 132, more preferably between 0.2 to 0.7 times a total thickness of the multilayer material 132. In this embodiment, the depth 126 is between 0.05 mm and 0.55 mm, preferably between 0.08 mm and 0.35 mm, more preferably between 0.1 mm and 0.2 mm. The reservoir 118 can be configured to contain various volumes of an allergen. In this embodiment, the reservoir 118 can hold a volume between 20 µl and 33 µl, preferably about 22 µl.

Table 1 shows dimensions of the test chamber according to some embodiments of the present invention.

TABLE 1

| Embodiment | Diameter (mm) I.O | Diameter (mm) O.D | Depth (mm) min | Depth (mm) max | Volume (µl) min | Volume (µl) max | Thickness (mm) min | Thickness (mm) max |
|---|---|---|---|---|---|---|---|---|
| #1 (8 mm) | 8 | 11 | 0.05 | 0.55 | 20 | 33 | 0.51 | 0.76 |
| #2 (12 mm) | 12 | 17 | 0.55 | 0.73 | 67 | 89 | 0.73 | 0.94 |
| #3 (18 mm) | 18 | 23 | 0.95 | 1.25 | 255 | 336 | 1.13 | 1.46 |

The patch test tape 102 can be formed of a hypoallergenic medical grade tape. The patch test tape 102 is preferably permeable to water vapor but water-resistant. In one embodiment, the patch test tape 102 includes the substrate layer 110 formed of a suitable material such as a polypropylene and the adhesive layer 114 formed of a skin-contact-grade adhesive that can adhere on the patient's skin like a second skin. Preferably, the patch test tape 102 is breathable to minimize skin irritation and provide sufficient adhesion against the skin to allow the patient to take a shower during the test period and also to enhance patents comfort. The cover sheet 106 is formed of a suitable material such as a polymeric material or a paper. The cover sheet 106 has a lower surface tension than the substrate layer 110 of the patch test tape 102 or coated with a release agent, such that the cover sheet 106 can release from the adhesive layer 108 without delaminating the adhesive layer 114 from the substrate layer 110.

To prepare the test unit 100 for a test, a tester loads each test chamber 104 with an allergen using an appropriate device, such as a syringe. If the patch test unit 100 is sold unassembled, the tester places a desired number of the test chambers 104 on the patch test tape 102 before loading of allergens. The tester may load each chamber 104 with a same allergen or different allergens. An amount of allergen can be critical to test results, so the appropriate amount is carefully determined and accurately loaded. The test chamber 104 is adapted to hold liquid allergens (both liquid and alcohol based), petrolatum based allergens, consumer products, and raw food allergens. The barrier layer 116 contains the allergen within the test chamber 104 and prevents the allergen from escaping through the side wall 128 or the chamber base 130. The barrier layer 116 also prevents any contaminants and/or fluids from entering the test chamber 104 during the test period (typically at least 48 hours).

Once the allergens are loaded, the cover 106 may be placed over the test chambers 104 until the tester is ready to place the patch test unit 100 on the patient. Alternatively, the patch test unit 100 may be placed on the patient immediately after the loading of the allergens. When the patch test unit 100 is placed on the patient, for example on the patient's back, the top edge 142 of the ridge 120 touches the patient's skin and slightly indents the skin as the tester lightly presses the patch test unit 100 onto the patient's back. The barrier layer 116 of the test chamber 104 is sufficiently rigid to sustain the pressure applied on the chamber base 130 and maintain the shape of the reservoir 118. Further, the ridge 120 maintains its shape as the test chamber 104 is lightly pressed against the patient's skin and throughout the test period (typically 48 hours). As stated previously, the ridge 120 temporarily indents the skin and creates a seal-like barrier, such that the allergen is contained within the test chamber 104 and contacts patient's skin.

The absorbent layer 112 absorbs or holds a liquid or petrolatum-based allergen, or consumer products, foods, etc. in the reservoir 118 while the patch test unit 100 is lifted and handled as the patch test unit 100 is applied on the patient. As such, the test chamber 104, which is formed from the multilayer material 132 including the absorbent layer 112, eliminates a tedious manual step of inserting an absorbent pad into a test chamber, and thus, eliminates any risk of contamination from mishandling of the absorbent pads. Further, since the test chamber 104 is formed from the multilayer material 132, wherein the absorbent layer 112 is permanently bonded to the barrier layer 116 via the adhesive layer 114, there is no risk of the absorbent layer 112 falling out from the test chamber 104.

Now that the patch test unit 100 including the test chamber 104 is described, exemplary non-limiting methods of making the test unit 100 will be explained.

In one embodiment, the multilayer material 132 used to form the test chamber 104, which includes the absorbent layer 112, the adhesive layer 114, and the barrier layer 116, may be provided by a supplier. Alternatively, materials for each layer 112, 114, 116 can be purchased separately and laminated to form the multilayer material 132. For example, a roll of a suitable fiber material, a roll of a suitable adhesive material, and a roll of a suitable plastic material are provided separately and laminated together to form a roll of the multilayer material 132. In a different embodiment, the roll of fiber material or the roll of plastic material may be coated with a suitable adhesive then laminated. Other conventional methods of making such a multilayer material 132 are also within the scope of the present invention. The multilayer material 132 may also be provided in sheets having various sizes. Although the test chamber 104 of FIGS. 1-4 are formed of the three-layer material 132, the test chamber 104 may be formed of multilayer materials including two layers or more than three layers in other embodiments. For example, a multilayer material may include more than one layer of paper or fiber material, and/or more than one layer of polymeric material, and more than one layer of adhesive to bond multiple layers together. In some embodiments, the absorbent layer 112 may be bonded to the barrier layer 116 without the adhesive layer 114. For example, a fiber layer may be melt spun or electrospun directly on the barrier layer 116.

Figure 4:
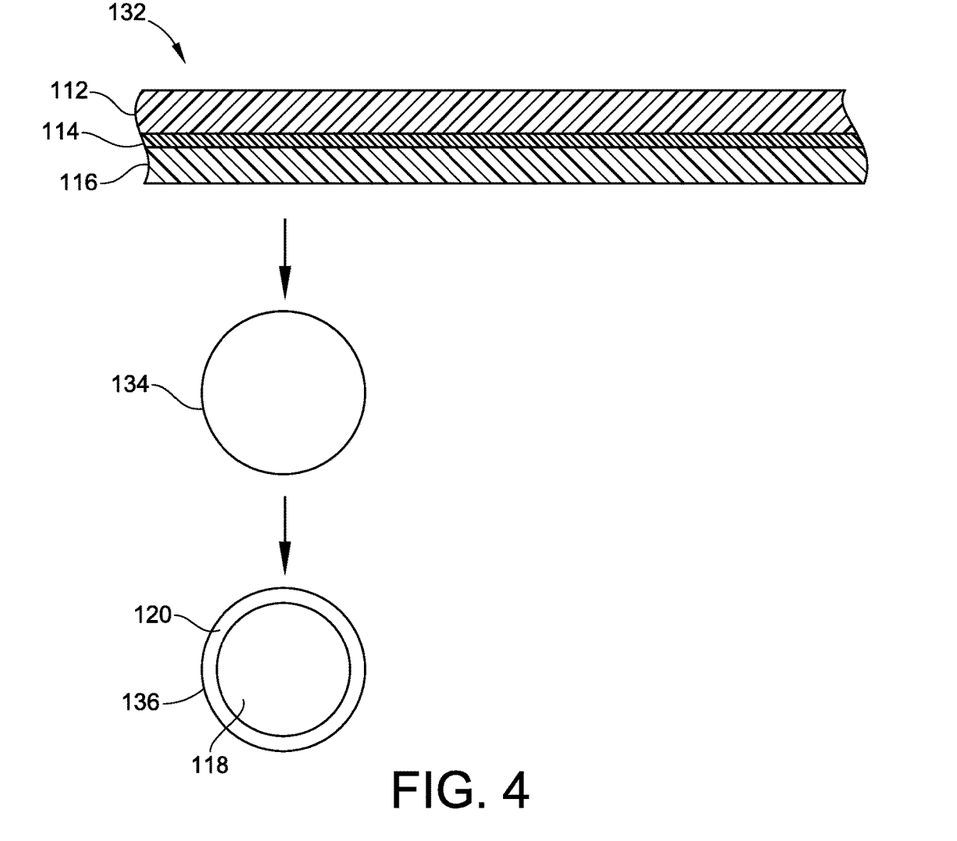
FIG. 4 is a schematic view of a process of forming the test chamber from a three-layer material according to an embodiment of the present invention.

As shown in FIG. 4, the multilayer material 132, which can be provided in a roll or a sheet, is punch cut to a flat disc 134. In this embodiment, the flat disc 134 has a circular shape to form a round-shaped test chamber 104. However, in other embodiments, the flat disc 134 may be cut to various shapes and sizes, such as a rectangle, triangle, etc., according to a desired shape of the test chamber. The flat disc 134 is then press embossed to form the test chamber 104 including the reservoir 118 and the ridge 120 using a suitable tool, such as a two (2) part forming tool set. The flat disc 134 is press embossed such that the absorbent layer 112 is in the innermost layer of the reservoir 118 to allow the absorbent layer 112 to come in contact with an allergen when the allergen is loaded in the test chamber 104.

In other embodiments, the multilayer material 132 can be press embossed or molded first to form the reservoir 118 and the ridge 120, then cut around an outer perimeter 136 to form the test chamber 104. Alternatively, the test chamber 104 may also be press embossed and cut simultaneously in a punch/embossing press. Other suitable tools, such as a rotary die, may also be used to cut and mold the test chambers 104.

Figure 5:
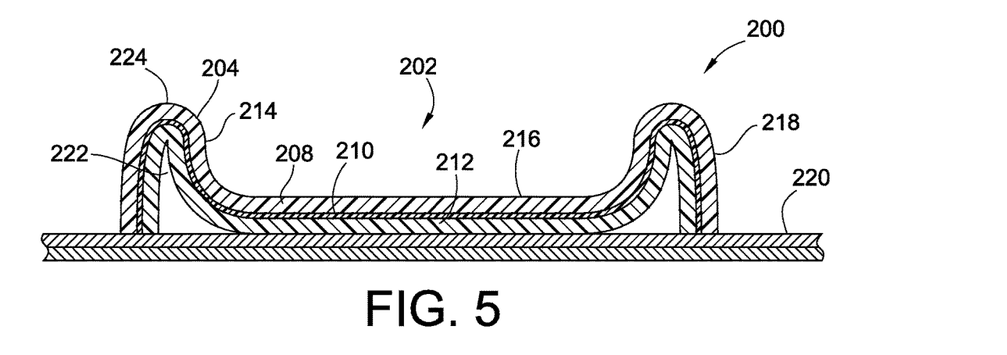
FIG. 5 is a schematic cross-sectional view (i.e. depth, thickness, etc. are not proportionally shown) of a test chamber according to an embodiment of the present invention.

FIG. 5 schematically shows a test chamber 200 according to a different embodiment of the present invention. The test chamber 200 is similar to the test chamber 104 and includes a reservoir 202 and a ridge 204. As it was with the test chamber 104, the test chamber 200 is a single piece device formed of a three-layer material including an absorbent layer 208, an adhesive layer 210, and a barrier layer 212. The reservoir 202 of the test chamber 200 is defined by an inner side 214 and a chamber base 216. In this embodiment, the inner side 214 tapers down to the chamber base 216. FIG. 5 illustrates the test chamber 204 schematically to exaggerate this smoother bend of the ridge 204, and thus, a depth and a thickness of the test chamber 204 are not proportionally shown here. An outer side 218 extends down from a curved top edge 224 of the ridge 204 to a patch test tape 220. A gap 222 is formed between the outer side 218 and the inner side 214, which increases from near the ridge 204 toward the patch test tape 220.

Figure 7:
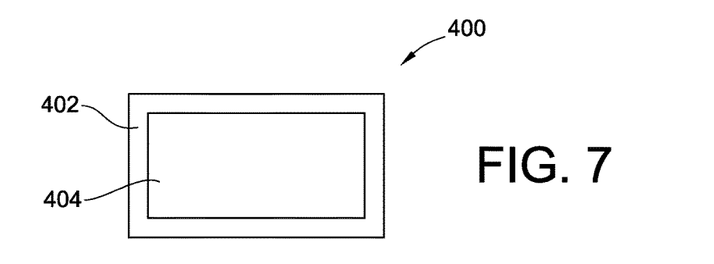
FIG. 7 is a schematic top view of a test chamber having a rectangular shape according to an embodiment of the present invention.
Figure 8:
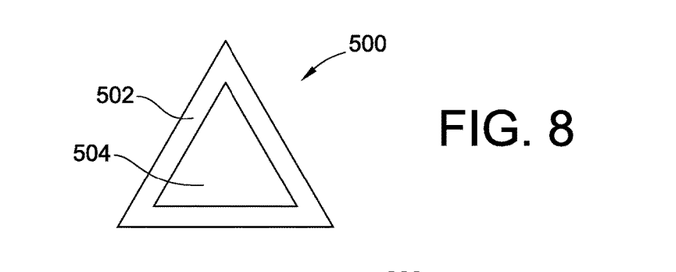
FIG. 8 is a schematic top view of a test chamber having a triangular shape according to an embodiment of the present invention.
Figure 9:
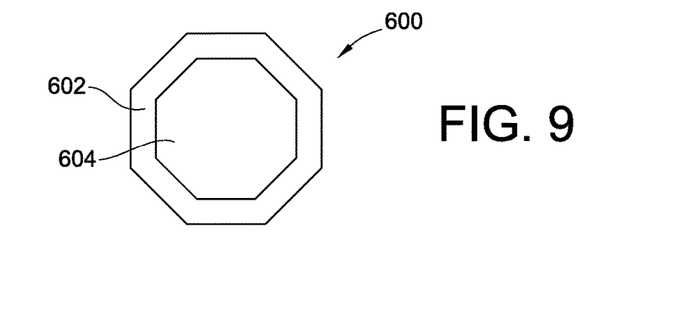
FIG. 9 is a schematic top view of a test chamber having an octagonal shape according to an embodiment of the present invention.

FIGS. 7-9 show a top view of test chambers 400, 500, 600 according to embodiments of the present invention. The test chambers 400, 500, 600 are similar to the test chambers 104, 200 of previously described embodiments in that they are a single piece device formed of a multilayer material including at least one absorbent layer, at least one adhesive layer, and at least one barrier layer. Each of the test chambers 400, 500, 600 includes a ridge 402, 502, 602, and a reservoir 404, 504, 604. As shown in FIGS. 7-9, the test chambers 400, 500, 600 have different geometric shapes. The test chamber 400 has a rectangular-shaped ridge 402. The test chamber 500 has a triangular shape ridge 502. The test chamber 600 has an octagonal-shaped ridge 502. In other embodiments, the test chamber can be formed to have various other shapes. Such different geometric shape test chambers can be helpful for distinguishing an allergic reaction from a skin irritation. The skin irritation normally will not appear in geometric shapes, whereas the allergic reaction to an allergen contained in a geometric shape test chamber will result in a skin reaction area corresponding to the geometric shape of the test chamber.

In one embodiment, a method of making an epicutaneous test chamber comprises steps of providing a multilayer material; cutting the multilayer material; and press forming the multilayer material to provide a test chamber including a reservoir and a ridge. The step of providing a multilayer material comprises laminating an absorbent material and a plastic material with an adhesive to provide a three-layer material including the absorbent layer, the adhesive layer, and the plastic material layer. The three-layer material can be provided in a roll form or a sheet. Further, the step of cutting the multilayer material includes punch cutting a flat disc from the three-layer material. The step of press forming includes press embossing the flat disc using a forming tool set, wherein the forming tool set press embosses a center area of the flat disc to provide a sunken negative space forming the reservoir. The pressed center area of the flat disc forms a chamber base and an inner side defining the reservoir, wherein the absorbent layer forms an inner surface of the reservoir. Further, a portion of the flat disc that forms the inner side is folded over to form the ridge including a top edge and an outer side. In some embodiments, the multilayer material is press formed and subsequently cut to form the test chamber. Alternatively, the multilayer material can be press formed and cut simultaneously to form the test chamber.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A single piece epicutaneous test chamber comprising:
   a reservoir having an inner surface formed of an absorbent material; and
   a ridge for contacting a test surface, the ridge surrounding the reservoir;
   wherein the reservoir and ridge are one continuous piece formed of the same material.

2. The test chamber of claim 1, wherein the single piece epicutaneous test chamber is formed of a multilayer material including at least one absorbent layer and at least one barrier layer, wherein the at least one absorbent layer and the at least one barrier layer are bonded by at least one adhesive layer, wherein one of at least one absorbent layer defines the inner surface of the reservoir.

3. The test chamber of claim 2, wherein the multilayer material comprises an absorbent layer formed of a cellulose fiber material having a thickness of between 0.006" and 0.010", an adhesive layer formed of a medical grade hypoallergenic adhesive having a thickness of between 0.001" and 0.002", and a barrier layer formed of a polyolefin material having a thickness of between 0.005" and 0.008".

4. The test chamber of claim 3, wherein a depth of the reservoir is between 0.33 mm to 0.55 mm; wherein the reservoir is configured to hold a volume between 20 µl and 33 µl.

5. The test chamber of claim 3, wherein the absorbent layer absorbs a liquid allergen loaded in the reservoir, and the barrier layer contains the liquid allergen within the reservoir and prevents the liquid allergen from escaping the reservoir.

6. The test chamber of claim 2, wherein the reservoir has a depth of between 0.3 to 1.5 times a thickness of the multilayer material.

7. The test chamber of claim 1, wherein the ridge includes an inner side, a top edge, and an outer side; wherein the reservoir is defined by a chamber base and the inner side; wherein the chamber base, the inner side, the top edge, and the outer side are one continuous piece; wherein the inner side vertically extends from the chamber base, and the top edge is formed on an end of the inner side opposite from the chamber base, wherein the ridge is configured to retain a shape against a patient's skin during a test period to contain an allergen within the reservoir.

8. The test chamber of claim 1, wherein the absorbent material is a paper.

9. The test chamber of claim 1, wherein the ridge has a circular shape.

10. The test chamber of claim 1, wherein the ridge has a rectangular shape.

11. The test chamber of claim 1, wherein the ridge has a triangular shape.

12. An epicutaneous test chamber comprising:
    a reservoir; and
    a ridge surrounding the reservoir;
    wherein the reservoir and the ridge are entirely integrally formed of a multilayer material including at least one absorbent layer and at least one barrier layer.

13. The test chamber of claim 12, wherein the reservoir and the ridge are formed of a continuous piece of the multilayer material, wherein one of the at least one absorbent layer defines an inner surface of the reservoir.

14. The test chamber of claim 13, wherein the reservoir is adapted to contain a liquid or a petrolatum-based allergen, wherein the absorbent layer defining the inner surface of the reservoir absorbs the liquid or the petrolatum-based allergen; wherein the ridge is configured to temporarily indent a patient's skin when the test chamber is placed on the patient with a light pressure and contains the allergen within the reservoir against the patient's skin during a 48 hour test period.

15. The test chamber of claim 12, wherein the multilayer material includes an absorbent layer, an adhesive layer, and a barrier layer, wherein the absorbent layer is permanently bonded to the barrier layer via the adhesive layer; wherein the absorbent layer defines the inner surface of the reservoir and a top surface of the ridge, wherein the top surface of the ridge contacts a patient's skin when the test chamber is applied on the patient; and wherein the barrier layer defines an outer surface of the reservoir.

16. The test chamber of claim 15, wherein the ridge comprises an inner side, a top edge, an outer side; wherein the reservoir is defined by a chamber base and the inner side; wherein the chamber base, the inner side, the top edge, and the outer side are continuously formed of the multilayer material; wherein the outer side extends vertically down from the top edge such that the barrier layer of the inner side and the barrier layer of the outer side faces each other, wherein the absorbent layer defines an outer surface of the outer side.

17. The test chamber of claim 12, wherein the reservoir has a depth of between 0.3 to 1.5 times a thickness of the multilayer material.

18. The test chamber of claim 12, wherein the multilayer material comprises an absorbent layer formed of a cellulose fiber material having a thickness of between 0.006" and 0.010", an adhesive layer formed of a medical grade hypoallergenic adhesive having a thickness of between 0.001" and 0.002", and a barrier layer formed of a polyolefin material having a thickness of between 0.005" and 0.008".

19. The test chamber of claim 17, wherein the reservoir has a depth of between 0.33 mm to 1.25 mm.

20. The test chamber of claim 12, wherein the ridge has a rectangular shape.

21. A paper test chamber for an epicutaneous patch test, comprising:
    a ridge for contacting a test surface, the ridge including an inner side, a top edge, and an outer side; and
    a reservoir defined by a chamber base and the inner side, wherein the reservoir is surrounded by the ridge;
    wherein the chamber base, the inner side, the top edge, and the outer side are formed of a paper.

22. The paper test chamber of claim 21, wherein the paper is a layer of a multilayer material, wherein the paper test chamber is press formed from the multilayer material.

23. The paper test chamber of claim 22, wherein the multilayer material comprises the paper layer bonded to a barrier layer by an adhesive layer.

24. The paper test chamber of claim 23, wherein the multilayer material comprises the paper layer formed of a cellulose fiber material having a thickness of between 0.006" and 0.010", the adhesive layer formed of a medical grade hypoallergenic adhesive having a thickness of between 0.001" and 0.002", and the barrier layer formed of a polyolefin material having a thickness of between 0.005" and 0.008".

25. The paper test chamber of claim 21, wherein the reservoir and the ridge are a single piece formed from a disc of a multilayer material, wherein the reservoir is configured to contain a liquid allergen or a petrolatum based allergen; wherein the reservoir has a depth of between 0.33 mm to 1.25 mm.

26. The paper test chamber of claim 21, wherein the ridge is configured to provide a barrier against a patient's skin to contain a liquid allergen or a petrolatum-based allergen within the reservoir, the ridge retaining a shape throughout a 48 hour test period.

27. The paper test chamber of claim 26, wherein the reservoir has a depth of between 1 to 3 times a thickness of the paper.

28. An epicutaneous patch test unit comprising:
a patch test tape;
at least one test chamber arranged on the patch test tape, the at least one test chamber formed entirely of a multilayer material including an absorbent layer; and
wherein the paper test chamber comprises a reservoir and a ridge, the ridge surrounding the reservoir.

29. The patch test unit of claim 28, wherein the reservoir and the ridge are formed of a continuous piece of the multilayer material, wherein the absorbent layer defines an inner surface of the reservoir.

30. The patch test unit of claim 29, wherein the reservoir is adapted to contain a liquid or a petrolatum-based allergen, wherein the absorbent layer defining the inner surface of the reservoir absorbs the liquid or the petrolatum based allergen; wherein the ridge is configured to temporarily indent a patient's skin when the patch test unit is placed on the patient with a light pressure and provide a barrier against the patient's skin to contain the allergen within the reservoir during a 48 hour test period.

31. The patch test unit of claim 30, wherein the patch test tape includes an adhesive layer formed of a skin contact grade adhesive; wherein plurality of the test chambers are arranged on top of the adhesive layer; wherein the patch test unit including the plurality of the test chambers loaded with allergens are placed on the patient such that the ridge touches the patient's skin; wherein the adhesive layer adheres to the patient's skin and holds the paper test chambers in place against the patient's skin; wherein the ridge is configured to retain a shape to continuously provide the barrier against the patient's skin to contain the allergen within the reservoir.

32. The patch test unit of claim 28, wherein the multilayer material includes an absorbent layer, an adhesive layer, and a barrier layer, wherein the absorbent layer is permanently bonded to the barrier layer via the adhesive layer; wherein the absorbent layer defines the inner surface of the reservoir and a top surface of the ridge, wherein the top surface of the ridge contacts a patient's skin when the patch test unit is applied on the patient; and wherein the barrier layer defines an outer surface of the reservoir.

33. The patch test unit of claim 32, wherein the test chamber has a round bowl-like shape; wherein the ridge include an inner side, a top edge, and an outer side; wherein the reservoir is defined by a chamber base and the inner side; wherein the chamber base, the inner side, the top edge, and the outer side are integrally formed of the multilayer material, where the outer side extends vertically down from the top edge such that the barrier layer of the inner side and the barrier layer of the outer side faces each other, wherein the absorbent layer defines an outer surface of the outer side.

34. The patch test unit of claim 28, wherein the reservoir has a depth of between 0.3 to 1.5 times a thickness of the multilayer material.

35. The patch test unit of claim 28, wherein the multilayer material comprises the absorbent layer formed of a cellulose fiber material having a thickness of between 0.006" and 0.010", an adhesive layer formed of a medical-grade hypoallergenic adhesive having a thickness of between 0.001" and 0.002", and a barrier layer formed of a polyolefin material having a thickness of between 0.005" and 0.008".

36. The patch test unit of claim 35, wherein the reservoir has a depth of between 0.33 mm to 0.55 mm.

37. The patch test unit of claim 28, wherein the ridge has a rectangular shape.

* * * * *